United States Patent
Eichert et al.

(10) Patent No.: US 12,369,027 B2
(45) Date of Patent: Jul. 22, 2025

(54) METHOD FOR AUTOMATICALLY UNBLOCKING OR BLOCKING A COMPUTER-SUPPORTED MEDICAL DEVICE

(71) Applicant: Siemens Healthcare Diagnostics Products GmbH, Marburg (DE)

(72) Inventors: Christof Eichert, Koenigstein (DE); Reza Golriz, Mainz (DE); Markus Preidel, Frankfurt (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 355 days.

(21) Appl. No.: 17/794,611

(22) PCT Filed: Jan. 25, 2021

(86) PCT No.: PCT/EP2021/051543
§ 371 (c)(1),
(2) Date: Jul. 21, 2022

(87) PCT Pub. No.: WO2021/151806
PCT Pub. Date: Aug. 5, 2021

(65) Prior Publication Data
US 2023/0064667 A1    Mar. 2, 2023

(30) Foreign Application Priority Data
Jan. 30, 2020 (EP) .................. 20154624

(51) Int. Cl.
*H04W 12/06* (2021.01)
*H04L 9/40* (2022.01)
(Continued)

(52) U.S. Cl.
CPC ............. *H04W 12/06* (2013.01); *H04L 63/08* (2013.01)

(58) Field of Classification Search
CPC ...... H04W 12/06; H04W 12/08; H04L 63/08; H04L 63/0853; G06F 21/35;
(Continued)

(56) References Cited

U.S. PATENT DOCUMENTS

2016/0217769 A1* 7/2016 Nguyen ............... G09G 5/30
2017/0085565 A1* 3/2017 Sheller ............... G06F 21/305
(Continued)

FOREIGN PATENT DOCUMENTS

| EP | 3087771 B1 | 6/2020 |
| JP | 2006352518 A | 12/2006 |
| WO | 2017110035 A1 | 6/2017 |

OTHER PUBLICATIONS

IP.com search history (Year: 2025).*

*Primary Examiner* — Moustapha Diaby
(74) *Attorney, Agent, or Firm* — Dugan & Dugan, PC

(57) ABSTRACT

Automatically blocking and/or unblocking a computer-supported medical device in a system includes the medical device and a mobile terminal. The mobile terminal comprises a first wireless communication device, and the medical device comprises a second wireless communication device. The medical device is automatically shifted from a blocked state into an unblocked state, if when the first communication device establishes a wireless connection with the second communication device and the signal strength of a signal of from the first communication device to the second communication device exceeds a first threshold. The medical device is automatically shifted from an unblocked state into a blocked state when the first communication device establishes a wireless connection with the second communication device and the signal strength of a signal from the first communication device to the second communication device falls below a second threshold and/or (Continued)

the wireless connection is interrupted for longer than a predetermined time interval.

20 Claims, 4 Drawing Sheets

(51) Int. Cl.
*H04W 12/08* (2021.01)
*H04W 12/12* (2021.01)
*H04W 88/02* (2009.01)

(58) Field of Classification Search
CPC ......... G06F 21/6245; G06F 2221/2111; A61B 5/150862; G01N 35/00623; G01N 35/00871; G01N 2035/00881
USPC ....................................................... 455/411
See application file for complete search history.

(56) References Cited

U.S. PATENT DOCUMENTS

| | | | |
|---|---|---|---|
| 2017/0302659 A1 | 10/2017 | Shteingart et al. | |
| 2017/0325091 A1 | 11/2017 | Freeman et al. | |
| 2019/0208421 A1* | 7/2019 | Ziraknejad | H04L 9/0825 |

\* cited by examiner

METHOD FOR AUTOMATICALLY UNBLOCKING OR BLOCKING A COMPUTER-SUPPORTED MEDICAL DEVICE

CROSS REFERENCE TO RELATED APPLICATIONS

This is a 371 of PCT/EP2021/051543, filed Jan. 25, 2021, which claims priority to European Patent Application No. EP 20154624.9, filed Jan. 30, 2020, both of which are hereby incorporated by reference herein in their entireties for all purposes.

FIELD

The invention relates to a method for automatically unblocking and/or blocking a computer-supported medical device in a system, the system comprising the computer-supported medical device and a mobile terminal.

BACKGROUND

Modern computer-supported medical devices, such as analysis instruments routinely used in analytics, forensics, microbiology, and clinical diagnostics, are capable of performing a large number of detection reactions and analyses with a large number of samples. In order to carry out a plurality of examinations automatically, various automatically operated devices are required for the spatial transfer of measurement cells, reaction vessels, and reagent liquid containers, such as transfer arms with a gripper function, conveyor belts, or rotatable transport wheels, as well as devices for transferring liquids, such as pipetting devices. The devices comprise a central control unit, which using appropriate software is able to plan and process the work steps for the desired analyses largely automatically.

Many of the analytical techniques used in such automated analysis instruments are based on optical methods. Measurement systems based on photometric (e.g., turbidimetric, nephelometric, fluorometric, or luminometric) or radiometric measurement principles are particularly widespread. These methods enable the qualitative and quantitative detection of analytes in liquid samples without the need for additional separation steps. The determination of clinically relevant parameters, such as the concentration or the activity of an analyte, is often carried out by extracting an aliquot, i.e., a partial quantity, of a patient's bodily fluid sample from a sample vessel using a pipetting device and transferring it to a reaction vessel. The aliquot of the sample is then also mixed with one or more test reagents in the reaction vessel by means of a pipetting device. A supply of the required reagents is kept in a number of reagent containers, which in turn are kept in a reagent container supply. By mixing the sample with the required reagent(s), a biochemical reaction is initiated that results in a measurable change in an optical property of the reaction batch.

The measurement result is then forwarded by the measuring system to a storage unit and evaluated. The analysis instrument then delivers sample-specific measurements to a user via an output medium such as a monitor, printer, or network connection.

Computer-supported medical devices often generate and/or process very sensitive personal health data, such as medical history data, laboratory values from bodily fluids, or data on genetic information, as well as other personal data such as name, date of birth, gender, or age. The data items are often linked to one another, so that particularly sensitive data records are created which require special technical protection measures, e.g., in order to prevent unauthorized access or manipulation as securely as possible.

In medical device technology, cyber security and data protection are becoming increasingly important. This is also reflected in sometimes increasingly stringent legal requirements, such as EU Regulation 2016/679 of the European Parliament and of the Council of 27 Apr. 2016 on the protection of natural persons with regard to the processing of personal data, on the free movement of such data and repealing Directive 95/46/EC (Basic Data Protection Regulation), among other things, to strengthen data protection in the handling of patient data.

However, in the often time-pressurized daily routine in laboratories, hospitals, and clinics, etc., it is sometimes observed that employees involved in operating medical devices, for example, in order to simplify work steps and save time, even dispense with basic safety measures, for example, they might not lock computers of medical devices with a password during short-term absences and disregard the appropriate work instructions. This allows unauthorized persons to easily gain access to sensitive data and can also lead to a risk of tampering with the data, which can have extremely serious medical consequences for the affected patients. In addition, the people involved and the institutions may be exposed to considerable legal and financial risks if binding standards are not always complied with.

Currently, the blocking and/or unblocking of computer-supported systems in the medical device sector is carried out manually by entering appropriate passwords.

SUMMARY OF THE INVENTION

It is therefore the object of the invention to provide tamper-resistant methods and means that enable the implementation of increased data protection requirements in the daily routine when operating computer-supported medical devices and ensure data integrity.

This object is achieved according to the invention by combining technologies with a mobile application for a method and automating the blocking and/or unblocking of a computer-supported medical device to the extent that this necessary security measure for data protection of users is taken for granted.

This has the advantage that increased data protection requirements for the operation of computer-supported medical devices can be implemented very reliably so that data integrity is ensured. At the same time, the workflow of medical device operation is greatly simplified and accelerated, and the likelihood of potential unauthorized access to patient data is reduced. Furthermore, the invention also makes it possible to access any number of a plurality of medical devices simultaneously and/or consecutively very quickly, which also simplifies and accelerates the workflow and thus increases efficiency. According to the invention, no specific mobile terminal is preferably required to execute the mobile application, but instead a commercially available smartphone, etc., can be used, which simplifies the implementation and increases its acceptance among the relevant users. This means that, particularly for stationary devices, a fast, user-friendly unblocking and/or blocking is possible, which in particular increases the usability of the devices and improves safety, also because the barrier to the actual use of blocking functions in everyday working routines is significantly reduced.

Thus, the subject matter of the present invention is, in particular, a method for automatically unblocking and/or blocking a computer-supported medical device in a system, the system comprising the computer-supported medical device and a mobile terminal, wherein the mobile terminal comprises a first wireless communication device for wirelessly transmitting and receiving data and wherein mobile application software can be executed by means of the mobile terminal, wherein the medical device comprises a device computer and wherein the device computer comprises a second wireless communication device for wirelessly transmitting and receiving data, wherein driver software can be executed on the device computer, which can establish a wireless communication connection to the first wireless communication device of the mobile terminal by means of the second communication device of the medical device, wherein the medical device is automatically transferred from a blocked state into an unblocked state if the first communication device of the mobile terminal has established a wireless connection to the second communication device of the medical device and the signal strength of the signal of the first communication device of the mobile terminal, received by the second communication device of the medical device, exceeds a predetermined first threshold value and/or the medical device is automatically transferred from an unblocked state into a blocked state if the first communication device of the mobile terminal has established a wireless connection to the second communication device of the medical device and the signal strength of the signal of the first communication device of the mobile terminal, received by the communication device of the medical device, falls below a predetermined second threshold value and/or if the wireless connection is interrupted for longer than a predetermined first time interval.

The invention is based on the consideration that a specially developed mobile application is executed on the user's mobile terminal, wherein the mobile terminal can advantageously be a smartphone, a tablet, and/or a smartwatch. The user preferably logs in to a designated authentication server with a username and password and is linked to the target system, e.g., the device computer, via the mobile application. The device computer has a transmitter hardware, preferably for one of the known wireless technologies, such as NFC (Near Field Communication), BLE (Bluetooth Low Energy), and/or Wi-Fi. The device computer runs dedicated driver software in the background that uses the available wireless technology to make the device visible to the mobile application. A special device identification token is preferably provided, which the mobile application needs to unlock the user. The signal strength is evaluated to determine whether a user is present nearby. This ensures that the device computer is only unblocked if the user is a predefined distance away, for example. If necessary, blocking will also advantageously be carried out in accordance with an appropriate pattern. An authentication server is preferably also provided that is responsible for managing users and devices. The user and the dedicated driver software login to this entity. The device computer can then be unblocked via this server.

In a preferred embodiment of the method according to the invention, the system further comprises an authentication service, wherein a wireless communication connection can be established from the mobile terminal with the first wireless communication device to the authentication service, and wherein a communication connection can be established between the device computer of the medical device and the authentication service, and wherein the unblocking and/or blocking of the medical device is carried out by means of the authentication service, wherein the authentication service preferably comprises an authentication server or is an authentication server. This has the advantage that appropriate authentication features, such as usernames and passwords, can be centrally managed via the authentication service. A particularly simple and efficient implementation of a method according to the invention is possible at the same time.

This preferably involves authenticating the mobile terminal and/or the device computer of the medical device on the authentication service.

The authentication of the mobile terminal preferably takes place via a wireless communication connection of the mobile terminal with the first communication device to the authentication service. This enables a particularly simple implementation of a method according to the invention.

Preferably, a user ID of the user is provided, which for example corresponds to or includes the user's username or is linked to the username. Preferably, the user ID is linked to one of a plurality of predefined user profiles, which assign predefined access rights to the respective user IDs. This has the advantage that access rights can be assigned and administered in a differentiated way, e.g., depending on the function of a specific user of a user group. This can further increase the level of security against unauthorized access, since users who do not require certain access rights for their respective activities and responsibilities do not receive them. This prevents, for example, inadvertent access to sensitive patient data by unauthorized users and/or the ability to delete and/or modify data.

Preferably, the authentication of the device computer of the medical device takes place via a communication connection of the device computer of the medical device to the authentication service.

Preferably, the mobile terminal comprises a smartphone or a portable computer, preferably a tablet computer, or the mobile terminal is a smartphone or a portable computer, preferably a tablet computer. The mobile device may also be a smartwatch or comprise a smartwatch. This has the advantage that widely used devices can be used as the mobile terminal, which are often carried by the operators of medical devices for other reasons, such as telephone availability or internet access. This makes it particularly simple and cost-effective to implement the method according to the invention. This also increases the acceptance among the operators, since no additional devices are required.

In particular, a combination of a plurality of mobile devices such as mobile phones and smartwatches can also be used. It is advantageous in this case that such combinations can be configured and adapted directly to customer requirements at any time.

Preferably, the automatic unblocking and/or blocking of the computer-supported medical device by means of a predetermined mobile terminal is only possible within a predetermined time interval. Preferably, the predefined time interval is, e.g., a working shift or, e.g., 8, 12, or 24 hours. This has the advantage that the user can login once using their corresponding access data at the beginning of their shift and then use the automatic unblocking or blocking function throughout the whole shift. At the end of the shift, the automatic unblocking or blocking function is automatically disabled again. This increases the security of the system and prevents misuse, e.g., by means of lost or mislaid mobile terminals by persons who are either not authorized or no longer authorized.

Preferably, the medical device is fixed or stationary and not directly portable like a mobile smartphone, for example, so that a user can always carry it directly about their person or in their clothing. Preferably, the medical device comprises an automatic analyzer, preferably an in-vitro analyzer for medical samples, preferably for blood. The medical device is particularly preferably an automatic analyzer, preferably an in-vitro analyzer for medical samples, preferably for blood. This makes it possible to implement increased data protection requirements in a very reliably way, including in locations such as medical laboratories.

The medical device preferably comprises a point-of-care system. Point-of-care systems are systems for medical testing at the point of treatment or near the point of treatment of a patient. Testing is therefore carried out at the site of the patient care and preferably at the same time as the patient care, for example, in a treatment room in a doctor's surgery, a hospital, a maternity clinic or, for example, in the case of emergency care, at the site of an accident or in an ambulance or rescue helicopter when transporting a patient. Alternatively, a point-of-care system can be used to provide patient care in the patient's home or at any other location where the patient is residing at the time the care is administered. Point-of-care systems can therefore be used in particular outside of special medical laboratories or central laboratories in close proximity to the patient, and tests can be carried out in real time during or soon after or before other examinations or treatments. The point-of-care system is preferably fixed or stationary and not directly portable like a mobile smartphone, for example, so that a user can always carry it directly about their person or in their clothing.

Preferably, the medical device comprises a system for intensive care. Intensive care systems are used, for example, in intensive care medicine, e.g., in intensive care units of hospitals or specially equipped vehicles or aircraft for patient transport. Preferably, the intensive care system is a syringe pump and/or infusion pump.

Preferably, the medical device comprises a medical imaging system. The imaging is preferably carried out in a medical imaging system, e.g., using X-rays (e.g. X-ray imaging, fluoroscopy, computed tomography), radionuclides (e.g., scintigraphy, positron emission tomography, single-photon emission computer tomography), ultrasound (e.g., sonography, color Doppler), magnetic resonance (e.g., magnetic resonance imaging), infrared radiation (e.g., diagnostic thermography), impedance (e.g., electrical impedance tomography) and/or visible light (e.g., endoscopy, optical tomography, video raster stereography).

Preferably, the first threshold value is assigned or corresponds to a first distance between the mobile terminal and the medical device, wherein the first distance is preferably less than 10 meters, particularly preferably less than 5 meters. Preferably, the first threshold value and/or the first distance depends on the size of the medical device. Preferably, the larger the medical device, the smaller the first threshold value. Accordingly, the first distance depends on the size of the medical device, wherein preferably the larger the medical device, the greater the distance. For example, in smaller point-of-care devices, which can be held in the hand or stand by the patient's bed, the first distance is preferably comparatively small and is only a few meters or even less than one meter, for example. For example, in large automation line systems and larger high-throughput analyzers in a central laboratory, the first distance is preferably comparatively large and is, for example, 10 meters or more. This makes it possible to select the respective threshold values or distances in such a way that they are adapted to the requirements of the respective medical devices and their operation.

Preferably, the second threshold value corresponds or is assigned to a second distance between the mobile terminal and the medical device, wherein the second distance is preferably less than 10 meters, particularly preferably less than 5 meters.

Preferably, the signal strength of the signal of the first communication device of the mobile terminal, received by the second communication device of the medical device, is assigned a corresponding distance between the mobile terminal and the medical device.

Preferably, the assignment between the first or second threshold value and the first or second distance between the mobile terminal and the medical device is based on the following estimation of the distance:

$$\text{Distance}=10\ \text{EXP}((\text{Signal\_strength}-\text{RSSI})/(10\ N)),$$

where EXP(X) stands for 10 raised to the power X, Signal_strength for the measured signal strength, RSSI for Received Signal Strength Indicator, and N for a constant to allow effective consideration of environmental influences, where N typically takes values from 2 to 4, preferably the value 2.

The first threshold value is preferably −60 dB to −70 dB, particularly preferably −60 dB. The latter value corresponds, for example, to a first distance of about one meter according to the above estimate for the distance.

The measured signal strength depends not only on the distance but also on the transmission strength (Broadcasting Power value). At maximum transmission strength (+4 dBm), the RSSI value ranges from approximately −26 (at a distance of a few centimeters) up to approximately −100 (at a distance of approximately 40 to 50 meters). The first time interval is preferably less than 3 minutes, particularly preferably less than 1 minute. This has the advantage that if the corresponding time interval is exceeded, an automatic blocking occurs. At the same time, however, it enables no blocking to take place in the event of very short interruptions of the connection due to, for example, short-term interference signals, and the operation is therefore more robust and less susceptible to interference.

Preferably, the first threshold value is lower than the second threshold value. The advantage of this is that the system is less susceptible to interference and unintentional, rapidly successive blocking or unblocking operations are avoided.

Preferably, the blocking comprises the disabling of a graphical user interface of an electronic display device of the medical device and/or the disabling of a user interface of the medical device for the input of commands. This has the advantage that the displayed data, in particular, sensitive patient data, cannot be viewed or manipulated by unauthorized third parties unsupervised.

Preferably, the unblocking comprises the enabling of a graphical user interface of an electronic display device of the medical device and/or the enabling of a user interface of the medical device for the input of commands. This has the advantage that the display device or user interface is immediately available to the user without any further measures, such as entering a password, and that waiting times are avoided, thus speeding up the overall workflow.

Another advantageous solution according to the invention involves a mobile terminal or a plurality of mobile terminals being learned and permanently configured only once by pairing, in a case similar to the so-called "Keyless GoTechnology" known from the automotive industry. Advantageously, according to the invention, the mobile terminal can also take the form of special transponders, such as those installed in corresponding car keys. However, according to the invention, such special requirements for additional hardware are advantageously not required.

Another object of the invention is a medical device comprising a device computer, the device computer comprising a second wireless communication device for wirelessly transmitting and receiving data, wherein the device computer is capable of running driver software which can establish a wireless communication connection to a first wireless communication device of a mobile terminal, the mobile terminal comprising the first wireless communication device for wirelessly transmitting and receiving data and wherein mobile application software can be executed by means of the second communication device of the medical device, wherein the device computer is configured in such a way that the medical device is automatically transferred from a blocked state into an unblocked state if the first communication device of the mobile terminal has established a wireless connection to the second communication device of the medical device and the signal strength of the signal of the first communication device of the mobile terminal, received by the second communication device of the medical device, exceeds a predetermined first threshold value and/or the medical device is automatically transferred from an unblocked state into a blocked state if the first communication device of the mobile terminal has established a wireless connection to the second communication device of the medical device and the signal strength of the signal of the first communication device of the mobile terminal, received by the communication device of the medical device, falls below a predetermined second threshold value and/or if the wireless connection is interrupted for longer than a predetermined first time interval.

Preferably, the medical device comprises an automatic analyzer, preferably an in-vitro analyzer for medical samples, preferably for blood. The medical device is particularly preferably an automatic analyzer, preferably an in-vitro analyzer for medical samples, preferably for blood.

Preferably, the medical device comprises a point-of-care system and/or an intensive care system and/or a medical imaging system. Preferably, the intensive care system is a syringe pump and/or infusion pump.

Another object of the invention is the use of a method according to the invention in a system, the system comprising a computer-supported medical device and a mobile terminal.

The medical device can preferably be, in particular, a diagnostic system for imaging procedures or in-vitro diagnostic devices.

BRIEF DESCRIPTION OF THE DRAWINGS

Exemplary embodiments of the invention are described in more detail with the aid of drawings. In the drawings.

Equivalent parts are labeled with the same reference signs in all figures.

DETAILED DESCRIPTION OF THE INVENTION

Figure 1:
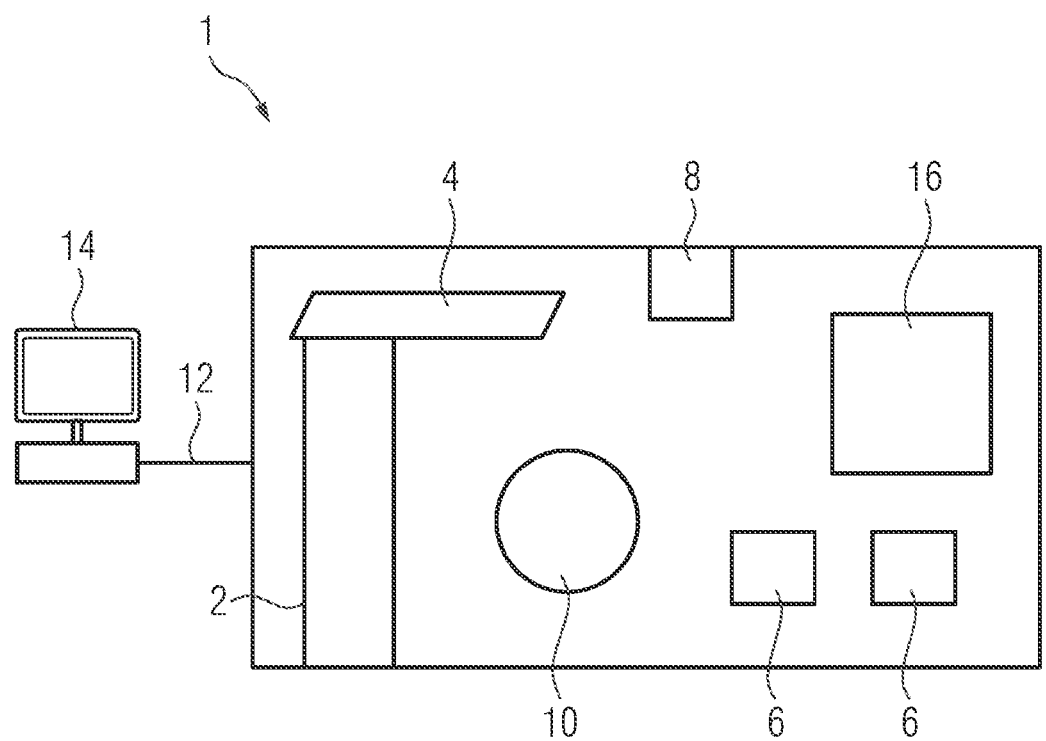
FIG. 1 shows a schematic illustration of a computer-supported medical device.

FIG. 1 shows a schematic illustration of a computer-supported medical device with some of the components it contains. The computer-supported medical device is an automatic analysis instrument 1. Here, only the most important components are presented in a highly simplified form, in order to explain the basic function of the automatic analysis instrument 1 without detailing the individual parts of each component.

The automatic analysis instrument 1 is designed to perform a wide range of blood and other bodily fluid analyses in a fully automated manner, without the need for any user activity. Instead, these are limited to maintenance or repair and refilling operations, for example, when cuvettes or reagents need to be refilled.

The sample vessels are fed to the automatic analysis instrument 1 on carriages, not shown in detail, in a supply rail 2. Information on the analyses to be carried out per sample can be transferred, for example, by means of bar codes attached to the sample vessels, which are read out in the automatic analysis instrument 1. Aliquots are taken from the sample vessels in a pipetting device 4 by means of a pipetting needle, not shown in detail. The aliquots are also fed to cuvettes not shown in detail, in which the actual analyses are carried out using a wide variety of measuring devices 6, such as photometers, etc. The cuvettes are taken from a cuvette supply 8. In addition, additional reagents, which are required depending on the analysis to be carried out, can be fed to the respective cuvette from a reagent container supply 10 by means of another pipette needle, not shown in detail.

The cuvettes are transported within the automatic analysis instrument 1 using transport devices not shown in detail here, such as transfer arms which can be moved in a variety of different spatial directions and have a gripping device for picking up the cuvettes. The entire process is controlled by a central control device, such as a computer 14 connected via a data line 12, supported by a plurality of additional electronic circuits and microprocessors, not illustrated in detail, within the automatic analysis instrument 1 and its components. The computer 14 also advantageously has a non-volatile memory in the form of a hard disk, a USB stick, or similar.

Figure 2:
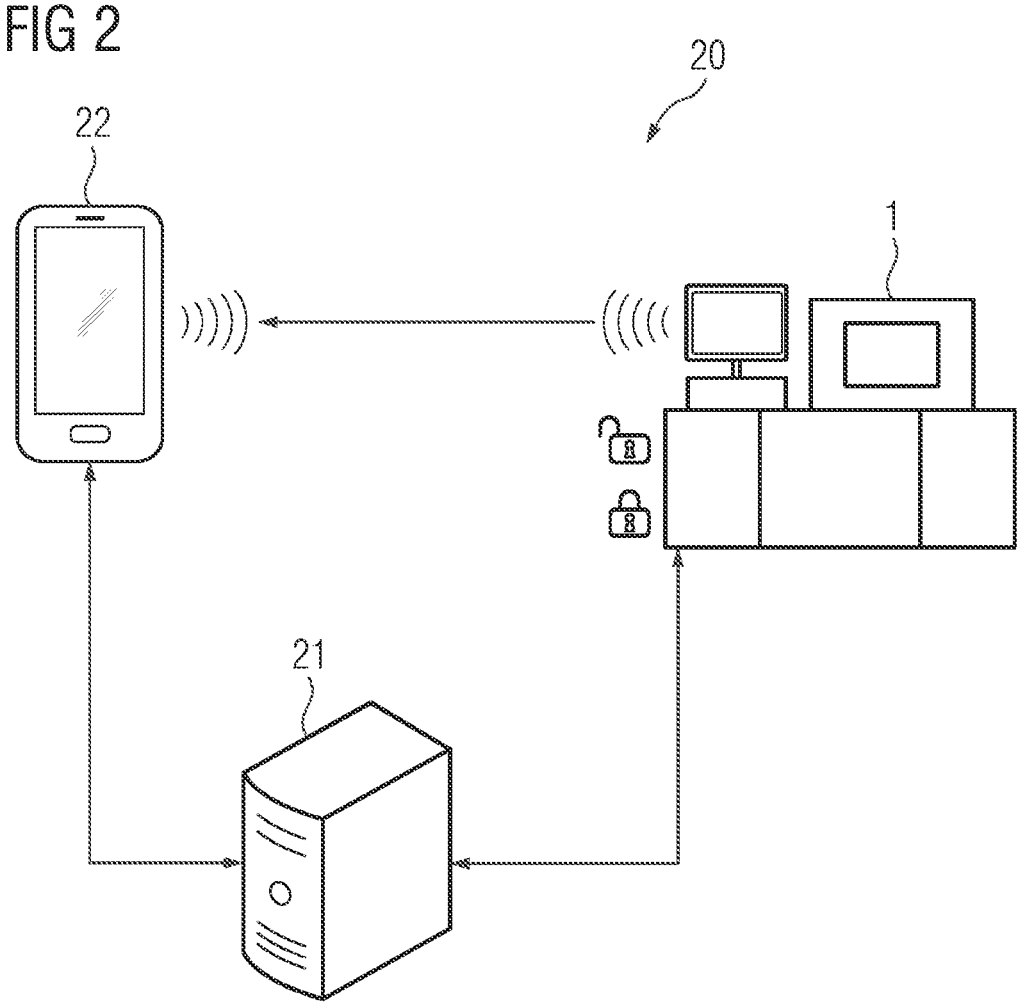
FIG. 2 shows a schematic illustration of a system comprising a computer-supported medical device, an authentication service, and a mobile terminal.

FIG. 2 shows a schematic illustration of a system 20 comprising a computer-supported medical device that is an automatic analyzer 1 and comprises a computer 14, an authentication service that is implemented as an authentication server 21, and a mobile terminal 22 that is a smartphone, tablet computer, or smartwatch. The mobile terminal 22 is designed and configured in such a way that it can be operated by a user, e.g., a trained laboratory technician. The system 20 comprises the following components. A specially developed mobile application is designed to run on the user's mobile device. The user must first login to a designated authentication server with a username and password. The user has also previously paired with the target system, i.e., the device computer, via the mobile application. The device computer has transmitter hardware, preferably for one or more wireless technologies, such as NFC (Near Field Communication), BLE (Bluetooth Low Energy), or Wi-Fi. The device computer runs dedicated driver software in the background that uses the available wireless technology to make the device visible to the mobile application. A special device identification token is provided, which the mobile application needs to unblock the user. The signal strength is evaluated to determine whether a user is present nearby. This ensures that the device computer is only unblocked if the user is a predefined distance away. The blocking also takes place according to a corresponding pattern. An authentication server is responsible for managing users and devices. The user and the dedicated driver software each login to this entity. A device computer is also unblocked via this server. FIG. 2 schematically shows corresponding data connections between the individual components of the system via arrows. The data connection between the mobile terminal and the automatic analyzer 1 is realized by wireless means.

Figure 3:
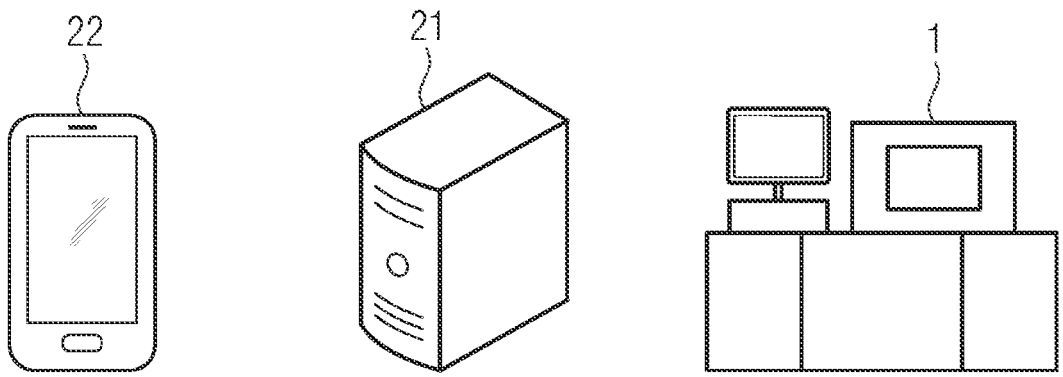
FIG. 3 shows a flow diagram of a method for device pairing.
Figure 3:
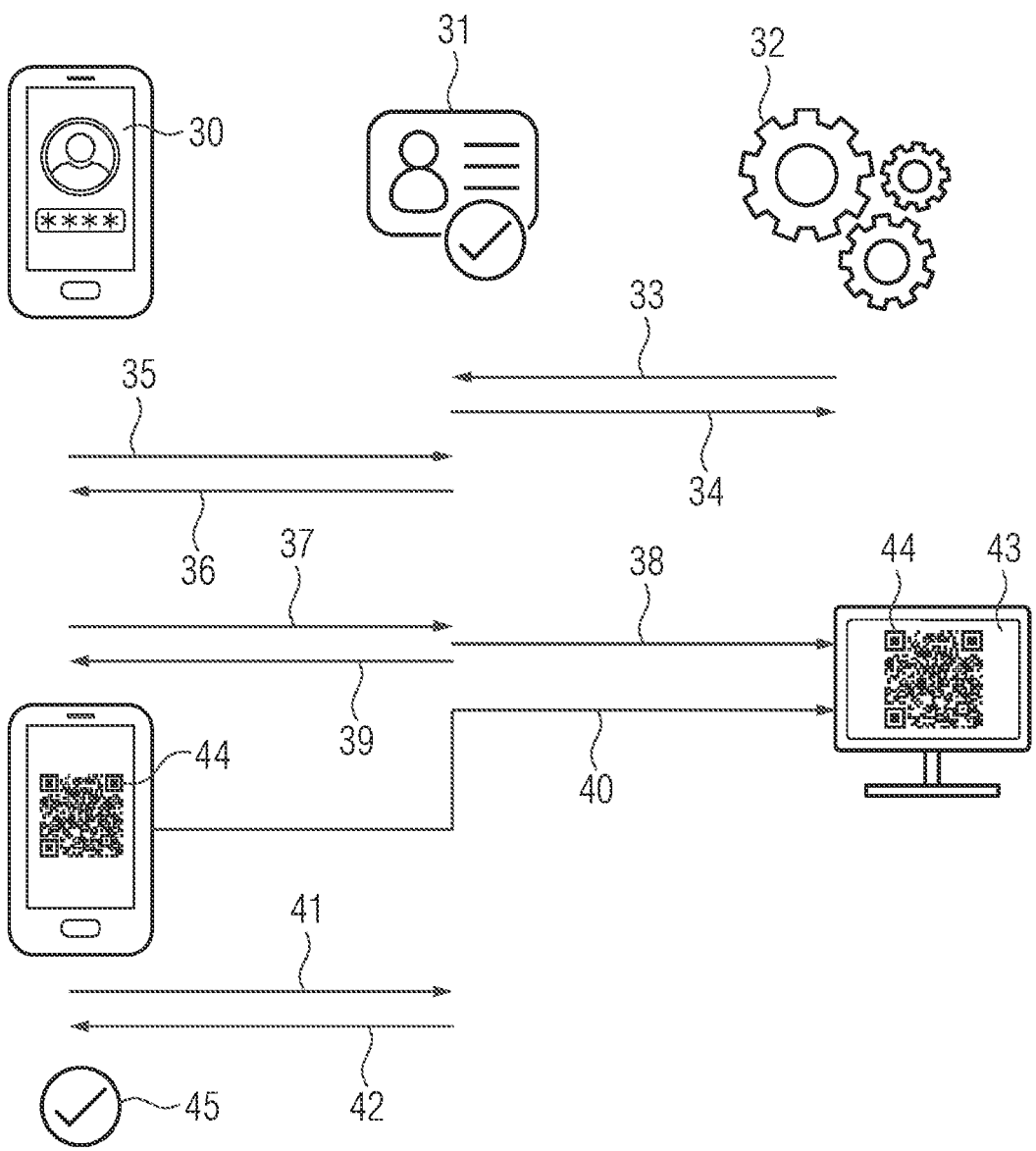

FIG. 3 shows a flow diagram of a method for device pairing. To ensure that the user has authorized access to the medical instrument, such as the automatic analysis instrument 1, an imaging diagnostic system, or other in-vitro diagnostic device, the user must first connect to the system using the pairing methods described below. This procedure must be performed once per device computer and user. In the next step, the dedicated driver software will advertise the device using the transmitter hardware. The device identification token is advertised. The user can use the mobile application to discover the systems in the environment. If the system is already paired, the user can login to the system using the method shown in FIG. 4 to unblock the device computer.

The flow diagram shown in FIG. 3 shows the three components: mobile terminal 22, authentication server 21, and an automatic analysis instrument 1 comprising a computer 14, also referred to as a device computer. A mobile application 30 runs on the mobile terminal 22. The authentication server 21 provides a corresponding web application 31. Dedicated driver software 32 runs on the device computer (computer 14). The device computer performs a device login with the web application 31 of the authentication server 21 and the authentication server 21 provides the device computer with a device identification token 34. The mobile terminal 22 also logs in to the web application 31 using the mobile application 30 (login 35) and the web application 31 provides the mobile terminal 22 with a session token 36. The mobile application 30 makes a pairing request 37 to the web application 31, which then causes a QR code 44 to be displayed on an electronic display device (monitor 43) of the device computer (Show QR code 38). The web application sends a request to the mobile application 30 to scan the QR code using the mobile terminal 22 (Scan QR code 40). A user then scans the QR code 44 displayed on the monitor 43 using the mobile terminal 22. The mobile application 30 sends the scanned QR code 44 (scanned QR code 41) to the web application 31, which in turn provides a device identification token 42 to the mobile application 30. This completes the device pairing 45.

Figure 4:
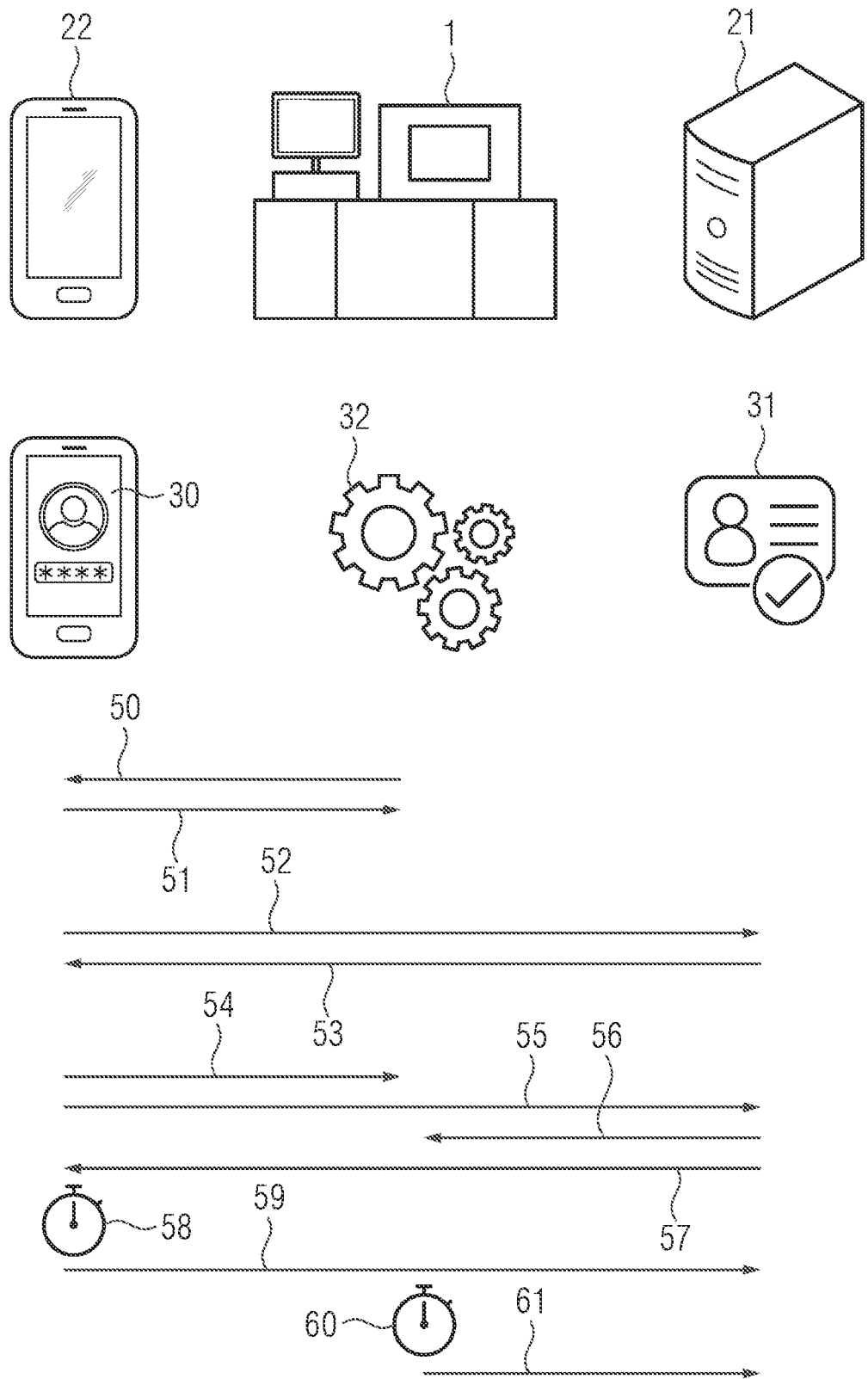
FIG. 4 shows a flow diagram of a method for unblocking a device computer of a computer-supported medical device.

FIG. 4 shows a flow diagram of a method for unblocking a device computer of a computer-supported medical device. After the device computer has been unblocked, the status of the connection is sent to the login server by the dedicated driver software and the mobile application at a predefined interval of a few minutes (e.g., 3 minutes). Among other things, the strength of the signal from both sides is determined and communicated. This information allows the login server to determine if the user is still in close proximity to the system or is further away. The distance may vary depending on the device type, for example, from a few meters for a smaller point-of-care device or 10 meters or more for a modular laboratory analysis system or a laboratory automation line. This data can be used to decide whether the device computer should be blocked or kept unblocked.

The flow diagram shown in FIG. 4 shows the three components: mobile terminal 22, authentication server 21, and an automatic analysis instrument 1 comprising a computer 14, also referred to as a device computer. A mobile application 30 runs on the mobile terminal 22. The authentication server 21 provides a corresponding web application 31. Dedicated driver software 32 runs on the device computer (computer 14). The device computer uses the driver software to make a request to advertise devices (Device advertising 50) via a wireless data connection to the mobile application 30 of the mobile device 22. The mobile application 30 searches for devices (Search for devices 51). The mobile application 30 sends a query to the web application 31 as to whether the device has been paired (Has device been paired? 52). Since the device is already paired, the web application sends a corresponding message to the mobile application 30 (Device is paired 53). The mobile application 30 then connects to the transmitter hardware of the device computer via a wireless data connection (Connect to transmitter hardware 54). The mobile application 30 sends a request to the web application 31 to unblock the device (Unblock device 55). The web application 31 is used to log in to the device computer as a user and to unblock the device computer or the automatic analysis instrument 1 (Log in with user and unblock 56). Next, the web application 31 informs the mobile application that the device computer or the automatic analysis instrument 1 has been unblocked (Device computer unblocked 57). At predefined time intervals 58, 60, the mobile application 30 and the device computer each send the current connection status to the web application 31 (Send connection status 59, 61).

LIST OF REFERENCE SIGNS 1 automatic analysis instrument
2 supply rail
4 pipetting device
6 measuring device
8 cuvette supply
10 reagent container supply
12 data line
14 computer
20 system
21 authentication server
22 mobile terminal
30 mobile application
31 web application
32 driver software
33 device login
34 device identification token
35 login
36 session token
37 pairing request
38 Show QR code
40 Scan QR code
41 scanned QR code
42 device identification token
43 monitor
44 QR code
45 Device pairing completed
50 Device advertising
51 Search for devices
52 Has device been paired?
53 Device is paired 54 Connect to transmitter hardware
55 Unblock device
56 Login with user and unblock
57 Device computer unblocked 60
58 time interval
59 Send connection status
60 time interval
61 Send connection status

The invention claimed is:

1. A method for automatically unblocking or blocking a computer-supported medical device in a system, the system comprising the computer-supported medical device and a mobile terminal, wherein the mobile terminal comprises a first wireless communication device for wirelessly transmitting and receiving data and wherein mobile application software can be executed by the mobile terminal, wherein the medical device comprises a device computer and wherein the device computer comprises a second wireless communication device for wirelessly transmitting and receiving data, wherein driver software can be executed on the device computer, which can establish a wireless communication connection to the first communication device of the mobile terminal via the second communication device of the medical device, the method comprising:
automatically transferring the medical device from a blocked state into an unblocked state in response to:
establishing a wireless connection from the first communication device of the mobile terminal to the second communication device of the medical device, and
determining that signal strength of a signal of the first communication device of the mobile terminal, received by the second communication device of the medical device, exceeds a predetermined first threshold value, wherein the first threshold value is predetermined based on the physical size of the medical device and the first threshold value is lower for a first medical device that is physically larger than a second medical device, and
automatically transferring the medical device from an unblocked state into a blocked state in response to:
establishing a wireless connection from the first communication device of the mobile terminal to the second communication device of the medical device, and
determining that the signal strength of the signal of the first communication device of the mobile terminal, received by the second communication device of the medical device, falls below a predetermined second threshold value or
determining that the wireless connection is interrupted for longer than a predetermined first time interval.

2. The method as claimed in claim 1, wherein the system further comprises an authentication service, wherein a wireless communication connection can be established from the mobile terminal with the first communication device to the authentication service, and wherein a communication connection can be established between the device computer of the medical device and the authentication service, and wherein the unblocking or blocking of the medical device is carried out by the authentication service, wherein the authentication service comprises an authentication server or is an authentication server.

3. The method as claimed in claim 2, wherein the mobile terminal or the device computer of the medical device is authenticated by the authentication service.

4. The method as claimed in claim 3, wherein the authentication of the mobile terminal takes place via a wireless communication connection of the mobile terminal with the first communication device to the authentication service.

5. The method as claimed in claim 3, wherein the authentication of the device computer of the medical device takes place via a communication connection of the device computer of the medical device to the authentication service.

6. The method as claimed in claim 1, wherein the mobile terminal comprises a smartphone, a tablet computer, or a portable computer.

7. The method as claimed in claim 1, wherein the medical device comprises an automatic analyzer.

8. The method as claimed in claim 1, wherein the first threshold value is assigned or corresponds to a first distance between the mobile terminal and the medical device, wherein the first distance is less than 10 meters.

9. The method as claimed in claim 8, wherein the second threshold value is assigned or corresponds to a second distance between the mobile terminal and the medical device, wherein the second distance is less than 10 meters.

10. The method as claimed in claim 9, wherein the first threshold value is less than the second threshold value.

11. The method as claimed in claim 9, wherein the first distance is less than 5 meters or the second distance is less than 5 meters.

12. The method as claimed in claim 1, wherein the first time interval is less than 3 minutes.

13. The method as claimed in claim 1, wherein:
the unblocking comprises enabling a graphical user interface of an electronic display device of the medical device or enabling a user interface of the medical device for the input of commands; or
the blocking comprises disabling the graphical user interface of the electronic display device of the medical device or disabling the user interface of the medical device for the input of commands.

14. The method as claimed in claim 1, wherein the first threshold value is assigned or corresponds to a first distance between the mobile terminal and the medical device, wherein the first distance is greater for a first medical device that is physically larger than a second medical device.

15. The method as claimed in claim 1, wherein the first time interval is less than 1 minute.

16. The method as claimed in claim 1, wherein the medical device comprises an in-vitro analyzer for medical samples including blood.

17. A medical device comprising a device computer, wherein the device computer is capable of executing driver software which can establish a wireless communication link to a first wireless communication device of a mobile terminal by a second wireless communication device of the device computer, the second wireless communication device for wirelessly transmitting and receiving data, wherein the mobile terminal comprises the first wireless communication device for wirelessly transmitting and receiving data and wherein mobile application software can be executed by the mobile terminal, wherein:
the device computer is configured such that the medical device is automatically transferred from a blocked state into an unblocked state in response to the first communication device of the mobile terminal establishing a wireless connection to the second communication device of the medical device and signal strength of a signal of the first communication device of the mobile terminal, received by the second communication device of the medical device, exceeding a predetermined first threshold value wherein the predetermined first threshold value is based on the physical size of the medical device and the first threshold value is lower for a first medical device that is physically larger than a second medical device, and the medical device is automatically transferred from an unblocked state into a blocked state in response to the first communication device of the mobile terminal establishing a wireless connection to the second communication device of the medical device and the signal strength of the signal of the first communication device of the mobile terminal, received by the second communication device of the medical device, falling below a predetermined second threshold value or the wireless connection is interrupted for longer than a predetermined first time interval.

18. The medical device as claimed in claim 17, wherein the medical device comprises an automatic analyzer.

19. The medical device as claimed in claim 17, wherein the medical device comprises an in-vitro analyzer for medical samples.

20. The medical device as claimed in claim 17, wherein the medical samples include blood.

\* \* \* \* \*